United States Patent [19]

Stoner

[11] Patent Number: 4,599,746
[45] Date of Patent: Jul. 15, 1986

[54] EYELID SHIELD AND METHOD OF MAKING SAME

[76] Inventor: Claudia C. Stoner, 314 Three Mile Course, Guilford, Conn. 06437

[21] Appl. No.: 665,726

[22] Filed: Oct. 29, 1984

[51] Int. Cl.⁴ .......................... A61F 9/00; A61F 13/12
[52] U.S. Cl. ................................................. 2/15; 2/12; 2/268; 2/DIG. 6; 128/163
[58] Field of Search ...................... 2/15, 12, 9, 2, 267, 2/268, DIG. 6; 128/132 R, 163

[56] References Cited

U.S. PATENT DOCUMENTS

| | | | |
|---|---|---|---|
| 2,165,668 | 7/1939 | Vaccaro | 2/15 |
| 2,243,982 | 6/1941 | Seely | 2/12 |
| 2,365,032 | 12/1944 | Wilkinson | 128/163 |
| 2,527,947 | 10/1950 | Loos | 2/15 X |
| 2,572,638 | 10/1951 | Loos | 2/15 X |
| 2,717,437 | 9/1955 | DeMestral | 2/DIG. 6 |
| 2,902,695 | 9/1959 | Werner | 2/268 |
| 3,068,863 | 12/1962 | Bowman | 2/15 X |
| 3,092,103 | 6/1963 | Mower | 2/15 X |
| 3,619,815 | 11/1971 | Towner | 2/12 |

*Primary Examiner*—Werner H. Schroeder
*Assistant Examiner*—J. L. Olds
*Attorney, Agent, or Firm*—William W. Jones

[57] ABSTRACT

A disposable shield for use in protecting the wearer's eyelids during sunbathing or other activities wherein glare and risk of sunburn are encountered. The shield is made from a fibrous material which absorbs mositure so as to cool the eyelid on which it is applied. The shield approximates the eyelid in size and is secured directly to the eyelid by a strip of releasable adhesive whereby the shield can be removed from the eyelid without any adhesive residue remaining behind on the eyelid.

6 Claims, 3 Drawing Figures

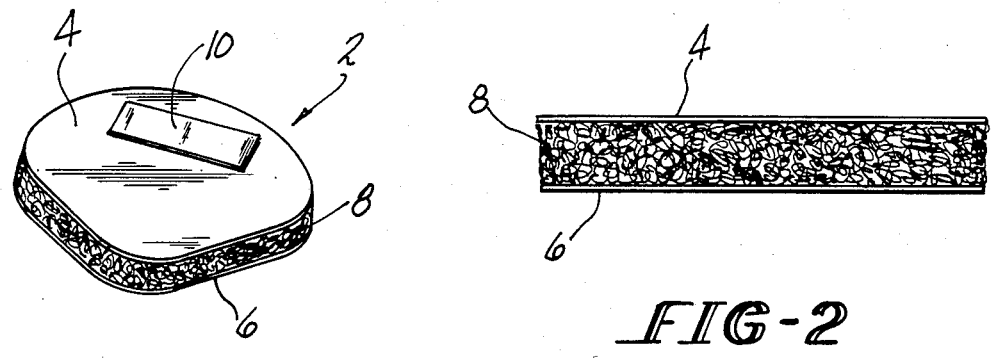
FIG-1
FIG-2
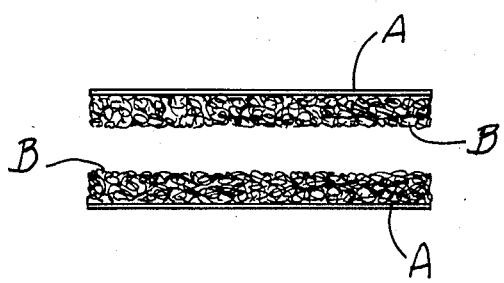
FIG-3

EYELID SHIELD AND METHOD OF MAKING SAME

This invention relates to a shield which can be applied directly to one's eyelids to protect the latter against glare and sunburn during sun bathing. The shield is capable of absorbing moisture from the eyelids and allows circulation of air through the shield material so that the wearer's eyelids remain comfortable.

Eye shields for use in protecting one's eyelids have been proposed in the prior art. U.S. Pat. No. 2,572,638 granted Oct. 23, 1951 to M. Loos discloses individual eyelid shields which are formed from fabric layers with an intermediate plastic layer which are wetted and pressed onto the wearer's eyelids. The wetting causes the shields to stick to the eyelids of the wearer. U.S. Pat. No. 3,068,863 granted Dec. 18, 1962 to C. L. Bowman discloses protective devices for wearing on one's eyelids, the device being formed from a fabric or plastic substance and having a releasable adhesive coating for securement to the skin of the wearer. U.S. Pat. No. 2,165,668 granted July 11, 1939 to G. Vaccaro discloses an eye protector having cotton pads with paper backing which is adhered to the wearer's face by adhesive tabs on opposite ends of the protector. U.S. Pat. No. 2,243,982, granted June 3, 1944 to R. C. Seeley, discloses a sanitary eyeshade formed from one or more layers of a fibrous material such as paper or the like. U.S. Pat. No. 3,619,815, granted Nov. 16, 1971 to D. D. Towner, Jr. discloses an eyelid shield which conforms to the shape of the eyelid and is secured thereto by a releasable adhesive and which is made from a highly flexible material such as plastic. One of the primary problems that the individual eyelid shields disclosed in the prior art have is that they do not make provision for the dissipation of perspiration which forms on the eyelids when the latter are covered by the shields, and, in fact, the prior art individual eyelid shields intensify perspiration of the eyelids. The prior art individual eyelid shields utilize plastic sheet material as a component layer and/or woven fabrics without taking into account the fact that the covered eyelids will tend to profusely perspire and the resultant perspiration will be irritating and uncomfortable to the wearer. Ideally, such perspiration must be dissipated so that the shields can be worn for a sufficiently long period of time to accomplish the sun bathing goals of the wearer.

The eyelid shields of this invention are made from a bulky fibrous material which has high moisture absorbancy and which is light weight and sufficiently opaque to provide the necessary sun screening capabilities. The material has a fibrous core layer which is formed from bulky fibers which are 70% wood pulp fibers and 30% polypropylene fibers. The core layer is highly moisture absorbant and will have a thickness of between about 250 grams per square meter and 380 grams per square meter. This ensures that the shields can be used for extended time periods without becoming saturated with perspiration. Both outer surfaces of the shields are formed from spun bonded polypropylene fiber sheets which are laminated onto the core layer. The surface polypropylene sheets are light weight, very smooth and soft, and pervious to moisture so that perspiration can pass from the skin through the surface sheets and into the core layer and can be evaporated from the core layer to the ambient atmosphere. The shields can be made from sheet material which has the surface spun bonded polypropylene liner forming one side of the sheet and the bulky fibrous wood pulp polypropylene layer forming one side of the sheet. Sheets of this type are placed with their bulky fibrous surfaces in face-to-face contact whereby the sheets will mat together and adhere to each other. Individual shields can then be die cut from the stock material. When the stock material is made in this fashion, the thickness of the bulky fibrous layer would be in the range of about 125 grams per square meter to about 190 grams per square meter, i.e., about one-half of the final thickness of the shields. One surface of each shield is provided with a tape strip bearing a peelable adhesive so that the shields can be peelably secured to the wearer's eyelids.

It is, therefore, an object of this invention to provide an improved eyelid shield for direct attachment to the eyelids during sunbathing.

It is an additional object of this invention to provide an eyelid shield of the character described which is moisture absorbant so as to absorb perspiration from the eyelids of the wearer.

It is a further object of this invention to provide an eyelid shield of the character described which has a moisture absorbant fibrous core layer and smooth moisture pervious outer layers.

These and other objects and advantages of the invention will become more readily apparent from the following detailed description of a preferred embodiment thereof when taken in conjunction with the accompanying drawings, in which:

FIG. 1 is a perspective view of an eyelid shield formed in accordance with this invention;

FIG. 2 is a side elevational view of the eyelid shield of FIG. 1; and

FIG. 3 is a side elevational view of two similar sheets of stock material which can be pressed together to form a stock sheet from which individual eyelid shields can be cut.

Referring now to the drawings, there is shown a preferred embodiment of an eyelid shield formed in accordance with this invention. The shield, denoted generally by the numeral 2, is generally ovate in shape so as to conform to the shape of the eyelid. It has an inner surface layer 4, an outer surface layer 6, and a core layer 8. A protected adhesive strip 10 is disposed on the inner surface layer 4, the strip 10 having a peelable nonadhesive cover which is removed prior to adhering the shield to one's eyelid. It will be noted that the core layer 8 is relatively thick, bulky and fibrous so as to provide for substantial moisture absorptive capabilities. Both of the surface layers 4 and 6 are, however, smooth, non-linty and devoid of dislodgable fibrils. Thus, the shield will not leave behind any fibrous material on one's eyelid after use. The shield's smooth surface layers provide a very comfortable cool feeling for the skin of the eyelid and also provide a readily printable surface whereby the outer surface layer 6 can be decorated or printed with a variety of indicia. The surface layers are sufficiently moisture permeable to allow passage of perspiration from the wearer's eyelids to the core layer and to allow evaporation of moisture from the core layer to the ambient atmosphere. Thus, the wearer's eyelids remain cool and dry while the shields are worn.

As seen in FIG. 3, the stock material for the shields can be formed from two sheets of similar stock, each of which has a smooth surface A and an opposite fibrous surface B. The fibrous surfaces B are oriented so as to face each other and the two sheets are pushed together to intermesh the two fibrous layers B.

The liner which forms the smooth outer surfaces of the shield is made by extruding polypropylene filaments from spinnerets and dropping the extruded filaments onto a moving wire. The matted filaments are then passed through a heated nip to form the final liner sheet. The sheet is smooth and moisture pervious. The fibrous wood pulp-polypropylene component is cast directly of the liner sheet and adheres thereto.

It will be readily appreciated that the eyelid shields of this invention are light weight and highly moisture absorbant. They provide the necessary protection from glare and sunburn and are smooth on their outer surfaces so as not to leave lint or the like on the eyelids of the wearer. They are formed from a composite of smooth porous outer liner sheets of polypropylene fibers and a core of a fibrous wood pulp and polypropylene mixture. The stock material from which the eyelid shields are made can be formed from a pair of like composite stock sheets each of which has a polypropylene liner sheet component and a fibrous wood pulp and polypropylene mixture component. The fibrous components of the two sheets are oriented facing each other and are then brought together as, for example, by passing them through a nip, whereupon they adhere to each other without the need of any adhesive.

Since many changes and variations of the disclosed embodiment of the invention may be made without departing from the inventive concept, it is not intended to limit the invention otherwise than as required by the appended claims.

What is claimed is:

1. An eyelid shield for direct attachment to one's eyelid, said shield providing sufficient opacity to protect the wearer's eyelids during sunbathing, said shield comprising outer surfaces consisting of sheets of spunbonded moisture permeable polypropylene fibers, which sheets are smooth and non-linty, and a core layer of bulky fibrous material consisting of a mixture of wood pulp fibers and polypropylene fibers which core layer is highly moisture absorbant, said outer surface sheets allowing passage of moisture from the wearer's eyelids to said core layer, and from said core layer to the ambient atmosphere; and circumscribed adhesive means on one of said outer surface sheets for peelably securing said shield solely to one's eyelid.

2. The eyelid shield of claim 1 wherein said core layer comprises about 70% wood pulp fiber and about 30% polypropylene fiber.

3. The eyelid shield of claim 1 wherein said core layer has a thickness in the range of about 250 gsm. and about 380 gsm.

4. The eyelid shield of claim 1 wherein said shield is formed from two sheets of material each having a spunbonded polypropylene sheet component and a bulky fibrous wood pulp polypropylene mixture component, said sheets of material being adhered together by matting each bulky fibrous layer to the other bulky fibrous layer.

5. A method for making eyelid shields adapted to be releasably secured directly to one's eyelids, said method comprising the steps of:

(a) providing a first sheet of stock material having a smooth, non-linty, moisture permeable spunbonded fibrous polypropylene sheet component, and a bulky, fibrous, moisture absorbant wood pulp fiber and polypropylene fiber mixture layer, said layers being adhered together with each layer defining an opposite surface of said first sheet;

(b) providing a second sheet of stock material having a smooth, non-linty, moisture permeable spunbonded fibrous polypropylene sheet component, and a bulky, fibrous, moisture absorbant wood pulp fiber and polypropylene fiber mixture layer, said layers being adhered together with each layer defining an opposite surface of said second sheet;

(c) orienting said first and second sheets to bring said bulky layers in each sheet into face-to-face alignment;

(d) joining said first and second sheets together by pressing said bulky layers in each sheet into each other to mat the bulky layers together to form a stock sheet having a bulky, fibrous, moisture absorbant core layer and opposed outer smooth, non-linty moisture permeable surface layers; and (e) cutting individual eyelid shields from said stock sheet.

6. A moisture absorbant eyelid shield for attachment directly to the wearer's eyelids for protecting the eyelids during sunbathing, said shield comprising:

(a) a first moisture permeably outer surface layer, said first outer surface layer being made from a smooth, non-linty material which is substantially non-moisture absorbant;

(b) a bulky, fibrous moisture absorbant core layer secured to said first outer surface layer;

(c) a second outer surface layer substantially identical to said first outer surface layer in composition, said second outer surface layer being secured to a side of said core layer opposite said first outer surface layer; and (d) releasable circumscribed adhesive means on one of said outer surface layers for peelably securing said shield solely to one's eyelids.

* * * * *